US011001852B1

(12) United States Patent
Brover et al.

(10) Patent No.: US 11,001,852 B1
(45) Date of Patent: May 11, 2021

(54) POLYNUCLEOTIDE SEQUENCES AND PROTEINS ENCODED THEREBY USEFUL FOR MODIFYING PLANT CHARACTERISTICS

(71) Applicant: CERES, INC., Thousand Oaks, CA (US)

(72) Inventors: Vyacheslav Brover, Simi Valley, CA (US); Timothy J. Swaller, Thousand Oaks, CA (US); Kenneth A. Feldmann, Newbury Park, CA (US); Maxim Troukhan, Agoura Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 71 days.

(21) Appl. No.: 16/185,866

(22) Filed: Nov. 9, 2018

Related U.S. Application Data

(60) Division of application No. 15/062,829, filed on Mar. 7, 2016, now Pat. No. 10,150,971, which is a continuation of application No. 13/626,508, filed on Sep. 25, 2012, now Pat. No. 9,309,573, which is a division of application No. 12/168,788, filed on Jul. 7, 2008, now Pat. No. 8,299,318.

(60) Provisional application No. 60/958,715, filed on Jul. 5, 2007.

(51) Int. Cl.
*C12N 15/82* (2006.01)
*A23L 11/00* (2021.01)
*A23L 27/10* (2016.01)
*C07K 14/415* (2006.01)
*A23L 7/10* (2016.01)
*C12Q 1/6895* (2018.01)
*A23L 19/00* (2016.01)

(52) U.S. Cl.
CPC ............ *C12N 15/8261* (2013.01); *A23L 7/10* (2016.08); *A23L 11/00* (2016.08); *A23L 19/00* (2016.08); *A23L 27/10* (2016.08); *C07K 14/415* (2013.01); *C12N 15/8242* (2013.01); *C12Q 1/6895* (2013.01); *C12Q 2600/158* (2013.01); *Y02A 40/146* (2018.01)

(58) Field of Classification Search
None
See application file for complete search history.

(56) References Cited

U.S. PATENT DOCUMENTS

| 7,834,244 | B2 | 11/2010 | Hu et al. |
| 2004/0172684 | A1 | 9/2004 | Kovalic et al. |
| 2009/0144847 | A1 | 6/2009 | Shaikh et al. |
| 2009/0276918 | A1 | 11/2009 | Choi et al. |
| 2011/0093981 | A9 | 4/2011 | La Rosa et al. |
| 2012/0216318 | A1 | 8/2012 | La Rosa et al. |

OTHER PUBLICATIONS

Kano-Murakami et al (1993, FEBS 334:365-368).*
Bowie et al, Science 247:1306-1310, 1990.*
McConnell et al, Nature 411 (6838):709-713, 2001.*
Hu et al., "Overexpressing a NAM, ATAF, and CUC (NAC) transcription factor enhances drought resistance and salt tolerance in rice," *PNAS* 103(35):12987-12992, 2006.
Kano-Murakami et al., "A rice homeotic gene, OSH1, causes unusual phenotypes in transgenic tobacco," *Federation of European Biochemical Societies* 334(3):365-368, 1993.
Bowie et al., "Deciphering the Message in Protein Sequences: Tolerance to Amino Acid Substitutions," *Science* 247:1306-1310, 1990.
McConnell et al., "Role of PHABULOSA and PHAVOLUTA in determining radial patterning in shoots," *Nature* 411:709-713, 2001.

* cited by examiner

*Primary Examiner* — Stuart F Baum
(74) *Attorney, Agent, or Firm* — Dentons US LLP

(57) ABSTRACT

The present invention relates to isolated nucleic acid molecules and their corresponding encoded polypeptides. The present invention further relates to the uses of these nucleic acid molecules and polypeptides. For example, the nucleic acid molecules and polypeptides could be used in making enzymes or used to make plants, plant cells, plant materials or seeds of a plant having such modulated growth or phenotype characteristics that are altered with respect to wild type plants grown under similar conditions.

19 Claims, No Drawings
Specification includes a Sequence Listing.

POLYNUCLEOTIDE SEQUENCES AND PROTEINS ENCODED THEREBY USEFUL FOR MODIFYING PLANT CHARACTERISTICS

CROSS REFERENCE PARAGRAPH

This application is a Divisional of application Ser. No. 15/062,829 filed on Mar. 7, 2016 (now U.S. Pat. No. 10,150,971), which application is a Continuation of application Ser. No. 13/626,508 filed on Sep. 25, 2012 (now U.S. Pat. No. 9,309,573), which is a Divisional of application Ser. No. 12/168,788 (now U.S. Pat. No. 8,299,318) filed Jul. 7, 2008, and for which priority is claimed under 35 U.S.C. § 120; and this application claims priority of U.S. Provisional Application No. 60/958,715 filed Jul. 5, 2007 under 35 U.S.C. § 119(e); the entire contents of each of which are hereby incorporated by reference.

FIELD OF THE INVENTION

The present invention relates to isolated nucleic acid molecules and their corresponding encoded polypeptides. The present invention further relates to using the nucleic acid molecules and polypeptides to make transgenic plants, plant cells, plant materials or seeds of a plant having modulated phenotypic and growth characteristics as compared to wild-type plants grown under similar conditions.

BACKGROUND OF THE INVENTION

Switchgrass is a hardy, warm season perennial bunch grass of the millet family. It was a component of the native prairie in the Great Plains states and Canada and can grow up to 1.8-2.2 m in height. Switchgrass propagates by rhizomes and seeds produced on spikelets. Switchgrass grown from seed has low vigor and is slow to establish, thus production is decreased until the third year growing year. Switchgrass uses the C4 carbon fixation pathway which allows for improved water use efficiency during its growth period, providing an advantage under drought and high temperature conditions. Once established, switchgrass is also tolerant of flooding and grows rapidly, capturing a significant amount of solar energy and turning it into stored energy in the form of cellulose.

As pasture forage, switchgrass is palatable in the vegetative stage and is grazed by certain animals, used as ground cover to control erosion and farmed as forage for livestock.

Switchgrass is also a good energy crop and can be cut and baled with conventional mowers and balers. Once established in a field, it can be harvested as a cash crop, either annually or semiannually, for 10 years or more before replanting is needed. Switchgrass offers important advantages as an energy crop, in part because it can be liquified, gasified, or burned directly. Ethanol production from switchgrass can provide as much as twenty times more net energy output than corn and removes considerably more $CO_2$ from the air. Switchgrass has the potential to produce the biomass required for production of up to 100 gallons (380 liters) of ethanol per metric ton, which gives switchgrass the potential to produce 1000 gallons of ethanol per acre, compared to 665 gallons for the sucrose from sugarcane and 400 gallons for the starch from corn.

Combustion of switchgrass pellets can result in nearly complete combustion with only 3% to 4% of original mass remaining as ash due in part to switchgrass' lower silica and chloride content as compared to cool season grasses. Ash contents can be further reduced by allowing switchgrass to overwinter in the field, thereby reducing the silica and chloride contents further through the process of leaching. There are also advantages from an ash content perspective to producing switchgrass in sandy soils as opposed to clay soils, again based on silica and chloride contents.

Despite the many advantages that switchgrass has as an energy crop, in order for this grass to fulfill its promise, new varieties of switchgrass are needed that will have increased hardiness and yield, reduce the need for nitrogen and other chemical fertilizers, and allow propagation under widely variant growing conditions.

Plants specifically improved for energy usage can be obtained using molecular technologies. Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, molecular genetics approaches that introduce and express recombinant nucleic acid molecules allow production of plant species tailored to grow more efficiently and produce more product in unique geographic and/or climatic environments. To this end, there is an ongoing need for genetic sequences and materials to advantageously manipulate plant characteristics such as architecture, biomass, development, composition, conversion efficiency, energy output, confinement, nitrogen use, nutrient uptake, phosphate use, photosynthetic capacity, shade avoidance, cold tolerance, drought tolerance, water use efficiency, stress tolerance, vigor, flowering time and yield to maximize the benefits of energy crops and other economically important crops depending on the benefit sought and the particular environment in which the crop must grow. These molecules may be from the plant itself, and simply expressed at a higher or lower level, or the molecules may be from different plant species.

SUMMARY OF THE INVENTION

The present invention, therefore, relates to isolated nucleic acid molecules and polypeptides and their use in making transgenic plants, plant cells, plant materials or seeds of plants having modulated plant characteristics, with respect to wild-type plants grown under similar or identical conditions, in traits such size (in whole or in part), vegetative growth, increased organ number and/or increased biomass (sometimes hereinafter collectively referred to as increased biomass), lethality, sterility, stress tolerance, or compositional characteristics as compared to a wild-type plant cultivated under identical conditions. (sometimes hereinafter collectively referred to as "modulated growth and phenotype characteristics").

Unless otherwise defined, all technical and scientific terms used herein have the same meaning as commonly understood by one of ordinary skill in the art to which this invention belongs.

DETAILED DESCRIPTION OF THE INVENTION

1. The Invention

The invention of the present application may be described by, but not necessarily limited to, the following exemplary embodiments.

The present invention discloses novel isolated nucleic acid molecules, nucleic acid molecules that interfere with these nucleic acid molecules, nucleic acid molecules that hybridize to these nucleic acid molecules, and isolated nucleic acid molecules that encode the same protein due to the degeneracy of the DNA code. Additional embodiments of the present application further include the polypeptides encoded by the isolated nucleic acid molecules of the present invention.

More particularly, the nucleic acid molecules of the present invention comprise: (a) a nucleotide sequence encoding an amino acid sequence that is at least 85% identical to any one of the polypeptides in the sequence listing (SEQ ID Nos. 1-9762), (b) a nucleotide sequence encoding an amino acid sequence that is at least 85% identical to any one of the polypeptides from *Panicum virgatum* in the sequence listing (SEQ ID Nos. 1-9176), (c) a nucleotide sequence that is complementary to any one of the nucleotide sequences according to (a) and (b), (d) a nucleotide sequence according to any one of the nucleotides in the sequence listing SEQ ID Nos. 1-9176, (e) a nucleotide sequence able to interfere with any one of the nucleotide sequences according to (a) and (b), (f) a nucleotide sequence able to form a hybridized nucleic acid duplex with the nucleic acid according to any one of paragraphs (a)-(d) at a temperature from about 40° C. to about 48° C. below a melting temperature of the hybridized nucleic acid duplex, (g) a nucleotide sequence encoding any one of the polypeptide sequences from *Panicum virgatum* in the sequence listing, (h) a nucleotide sequence encoding any one of the polypeptide sequences given in the sequence listing.

The present invention further embodies a vector comprising a first nucleic acid having a nucleotide sequence encoding a plant transcription and/or translation signal, and a second nucleic acid having a nucleotide sequence according to the isolated nucleic acid molecules of the present invention. More particularly, the first and second nucleic acids may be operably linked. Even more particularly, the second nucleic acid may be endogenous to a first organism, and any other nucleic acid in the vector may be endogenous to a second organism. Most particularly, the first and second organisms may be different species.

In a further embodiment of the present invention, a host cell may comprise an isolated nucleic acid molecule according to the present invention. More particularly, the isolated nucleic acid molecule of the present invention found in the host cell of the present invention may be endogenous to a first organism and may be flanked by nucleotide sequences endogenous to a second organism. Further, the first and second organisms may be different species. Even more particularly, the host cell of the present invention may comprise a vector according to the present invention, which itself comprises nucleic acid molecules according to those of the present invention.

In another embodiment of the present invention, the isolated polypeptides of the present invention may additionally comprise amino acid sequences that are at least 85% identical to any one of the polypeptides in the sequence listing.

Other embodiments of the present invention include methods of introducing an isolated nucleic acid of the present invention into a host cell. More particularly, an isolated nucleic acid molecule of the present invention may be contacted to a host cell under conditions allowing transport of the isolated nucleic acid into the host cell. Even more particularly, a vector as described in a previous embodiment of the present invention, may be introduced into a host cell by the same method.

Methods of detection are also available as embodiments of the present invention. Particularly, methods for detecting a nucleic acid molecule according to the present invention in a sample. More particularly, the isolated nucleic acid molecule according to the present invention may be contacted with a sample under conditions that permit a comparison of the nucleotide sequence of the isolated nucleic acid molecule with a nucleotide sequence of nucleic acid in the sample. The results of such an analysis may then be considered to determine whether the isolated nucleic acid molecule of the present invention is detectable and therefore present within the sample.

A further embodiment of the present invention comprises a plant, plant cell, plant material or seeds of plants comprising an isolated nucleic acid molecule and/or vector of the present invention. More particularly, the isolated nucleic acid molecule of the present invention may be exogenous to the plant, plant cell, plant material or seed of a plant.

A further embodiment of the present invention includes a plant regenerated from a plant cell or seed according to the present invention. More particularly, the plant, or plants derived from the plant, plant cell, plant material or seeds of a plant of the present invention preferably has increased size (in whole or in part), increased vegetative growth, increased organ number and/or increased biomass (sometimes hereinafter collectively referred to as increased biomass), lethality, sterility, improved stress tolerance, or compositional characteristics as compared to a wild-type plant cultivated under identical conditions. Furthermore, the transgenic plant may comprise a first isolated nucleic acid molecule of the present invention, which encodes a protein involved in modulating growth and phenotype characteristics, and a second isolated nucleic acid molecule which encodes a promoter capable of driving expression in plants, wherein the growth and phenotype modulating component and the promoter are operably linked. More preferably, the first isolated nucleic acid may be mis-expressed in the transgenic plant of the present invention, and the transgenic plant exhibits modulated characteristics as compared to a progenitor plant devoid of the nucleic acid, when the transgenic plant and the progenitor plant are cultivated under identical environmental conditions. In another embodiment of the present invention the modulated growth and phenotype characteristics may be due to the inactivation of a particular sequence, using for example an interfering RNA.

A further embodiment consists of a plant, plant cell, plant material or seed of a plant according to the present invention which comprises an isolated nucleic acid molecule of the present invention, wherein the plant, or plants derived from the plant, plant cell, plant material or seed of a plant, has the modulated growth and phenotype characteristics as compared to a wild-type plant cultivated under identical conditions.

Another embodiment of the present invention includes methods of modulating growth and phenotype characteristics in plants. More particularly, these methods comprise transforming a plant with an isolated nucleic acid molecule according to the present invention.

In yet another embodiment, lethality genes of the invention can be used to control transmission and expression of transgenic traits, thereby facilitating the cultivation of transgenic plants without the undesired transmission of transgenic traits to other plants. Such lethality genes can also be utilized for selective lethality, by combining the lethal gene with appropriate promoter elements for selective expression, to thereby cause lethality of only certain cells or only under certain conditions.

In another aspect, methods of identifying a trait associated polymorphism are provided. The methods include providing a population of switchgrass plants, and determining whether one or more polymorphisms in the population are present within a nucleic acid corresponding to a switchgrass polynucleotide provided in the Sequence Listing. The correlation between variation in the trait in a tissue in plants of the population and the presence of the one or more polymorphisms in plants of the population is measured, thereby permitting identification of the trait associated polymorphism. The trait may be selected from a feature noted in the Sequence Listing for a polypeptide encoded by the corresponding switchgrass polynucleotide.

2. Definitions

The following terms are utilized throughout this application:

Biomass: As used herein, "biomass" refers to useful biological material including a product of interest, which material is to be collected and is intended for further processing to isolate or concentrate the product of interest. "Biomass" may comprise the fruit, or parts of it, or seeds, leaves, or stems or roots where these are the parts of the plant that are of particular interest for the industrial purpose. "Biomass", as it refers to plant material, includes any structure or structures of a plant that contain or represent the product of interest.

Transformation: Examples of means by which this can be accomplished are described below and include *Agrobacterium*-mediated transformation (of dicots (9-10), of monocots (11-13), and biolistic methods (14)), electroporation, in planta techniques, and the like. Such a plant containing the exogenous nucleic acid is referred to here as a $T_0$ for the primary transgenic plant and $T_1$ for the first generation.

Functionally Comparable Proteins or Functional Homologs: This phrase describes a set of proteins that perform similar functions within an organism. By definition, perturbation of an individual protein within that set (through misexpression or mutation, for example) is expected to confer a similar phenotype as compared to perturbation of any other individual protein. Such proteins typically share sequence similarity resulting in similar biochemical activity. Within this definition, homologs, orthologs and paralogs are considered to be functionally comparable.

Functionally comparable proteins will give rise to the same characteristic to a similar, but not necessarily the same, degree. Typically, comparable proteins give the same characteristics where the quantitative measurement due to one of the comparables is at least 20% of the other, more typically, between 30 to 40%; even more typically, between 50-60%; even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if another filler sequence is placed between them. Thus, the promoter and coding sequences of a corn gene expressing an amino acid transporter are not heterologous to each other, but the promoter and coding sequence of a corn gene operatively linked in a novel manner are heterologous.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene coding region from a different plant species or from a non-plant organism.

Percentage of sequence identity: As used herein, the term "percent sequence identity" refers to the degree of identity between any given query sequence and a subject sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) Nucleic Acids Res. 31(13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

To determine a percent identity for polypeptide or nucleic acid sequences between a query and a subject sequence, the sequences are aligned using Clustal W and the number of identical matches in the alignment is divided by the query length, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some embodiments, the amino acid sequence of a suitable subject polypeptide has greater than 40% sequence identity (e.g., >40%, >50%, >60%, >70% or >80%, >90%, 91%, >92%, >93%, >94%, >95%, >96%, >97%, >98%, or >99%) to the amino acid sequence of the query polypeptide.

In other embodiments, the nucleotide sequence of a suitable subject nucleic acid has greater than 40% sequence identity (e.g., >45%, >50%, >55%, >60%, >65%, >70%, >75%, >80%, >90%, >91%, >92%, >93%, >94%, >95%, >96%, >97%, >98%, or >99%) to the nucleotide sequence of the query nucleic acid.

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m$-5° C. to $T_m$-10° C. Medium or moderate stringency conditions are those providing $T_m$-20° C. to $T_m$-29° C. Low stringency conditions are those providing a condition of $T_m$-40° C. to $T_m$-48° C. The relationship between hybridization conditions and $T_m$ (in ° C.) is expressed in the mathematical equation:

$$T_m = 81.5 - 16.6(\log_{10}[Na^+]) + 0.41(\% \text{ G+C}) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log\{[Na^+]/(1+0.7[Na^+])\} + 0.41(\% \text{ G+C}) - 500/L\ 0.63(\% \text{ formamide}) \quad (II)$$

where L represents the number of nucleotides in the probe in the hybrid (Bonner et al. (1973) *J. Mol. Biol.* 81:123). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) *J. Mol Biol,* 170: 827-842), stringency conditions can be adjusted to favor detection of identical genes or related family members.

Equation II is derived assuming the reaction is at equilibrium. Therefore, hybridizations according to the present invention are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

3. Important Characteristics of the Polynucleotides and Polypeptides of the Invention The nucleic acid molecules and polypeptides of the present invention are of interest because when the nucleic acid molecules are mis-expressed (i.e., when expressed at a non-natural location or in an increased or decreased amount relative to wild-type) they produce plants that exhibit modulated growth and phenotype characteristics as compared to wild-type plants. This trait can be used to exploit or maximize plant products. For example, the nucleic acid molecules and polypeptides of the present invention are used to increase the expression of genes that cause the plant to have modulated growth and phenotype characteristics.

Because some of the disclosed sequences and methods increase vegetative growth, the disclosed methods can be used to enhance biomass production. For example, plants that grow vegetatively have an increase biomass production, compared to a plant of the same species that is not genetically modified for substantial vegetative growth. Examples of increases in biomass production include increases of at least 5%, at least 10%, at least 20%, or even at least 50%, when compared to an amount of biomass production by a plant of the same species not genetically modified.

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase (12) where the floral organs are produced. If the appropriate environmental and developmental signals for floral, or reproductive, growth are disrupted, the plant will not be able to enter reproductive growth, therefore maintaining vegetative growth and increasing overall biomass.

As more and more transgenic plants are developed and introduced into the environment, it can be important to control the undesired spread of the transgenic triat(s) from transgenic plants to other traditional and transgenic cultivars, plant species and breeding lines, thereby preventing cross-contamination. Such genetic confinement systems (also called biocontainment applications) can be designed using a number of different technical strategies. The use of a conditionally lethal gene, i.e. one which results in plant cell death under certain conditions, has been suggested as a means to selectively kill plant cells containing a recombinant DNA (see e.g., WO 94/03619 and US patent publication 20050044596A1). The use of genes to control transmission and expression of transgenic traits is also described in (see US patent publication 20050257293A1), which is hereby incorporated by reference. Some of the nucleotides of the invention are lethal genes, and can therefore be used as conditionally lethal genes, namely genes to be expressed in response to specific conditions, or in specific plant cells. For example, a gene that encodes a lethal trait can be placed under that control of a tissue specific promoter, or under the control of a promoter that is induced in response to specific conditions, for example, a specific chemical trigger, or specific environmental conditions.

Male or female sterile genes can also be used to control the spread of certain germplasm, such as by selective destruction of tissue, such as of the tapetum by fusing such a gene to a tapetum-specific promoter such as, TA29. Further examples of such promoters are described below.

The sequences of the invention can be used to advantageously manipulate plant characteristics in traits such as size (in whole or in part), vegetative growth, increased organ number and/or increased biomass (sometimes hereinafter collectively referred to as increased biomass), lethality, sterility, stress tolerance, or compositional characteristics as compared to a wild-type plant cultivated under identical conditions. Furthermore, the sequences of the invention can be used to advantageously manipulate plant characteristics such as architecture, biomass, development, composition, conversion efficiency, energy output, confinement, nitrogen use, nutrient uptake, phosphate use, photosynthetic capacity, shade avoidance, cold tolerance, drought tolerance, water use efficiency, stress tolerance, vigor, flowering time and yield to maximize the benefits of energy crops and other economically important crops depending on the benefit sought and the particular environment in which the crop must grow. These molecules may be from the plant itself, and simply expressed at a higher or lower level, or the molecules may be from different plant species The sequences of the invention can be applied to substrates for use in array applications such as, but not limited to, assays of global gene expression, under varying conditions of development, and growth conditions. The arrays are also used in diagnostic or forensic methods.

The polynucleotides of the invention are also used to create various types of genetic and physical maps of the genome of switchgrass plants. Some are absolutely associated with particular phenotypic traits, allowing construction of gross genetic maps. Creation of such maps is based on differences or variants, generally referred to as polymorphisms, between different parents used in crosses. Common methods of detecting polymorphisms that can be used are restriction fragment length polymorphisms (RFLPs, single nucleotide polymorphisms (SNPs) or simple sequence repeats [(SSRs), also called microsatellites].

The sequence information disclosed herein can be useful in breeding of switchgrass plants. Based on the information in the Sequence Listing, one can search for and identify polymorphisms linked to genetic loci for such polypeptides. As those of skill in the art appreciate, polymorphisms can be identified based on characterization of libraries, such as genomic or expression libraries, and/or characterization of nucleic acids extracted from individual plants, and possibly amplified and/or otherwise processed. For example, the nucleotide sequences provided in the sequence listing can serve for design of primers for amplification of nucleic acids and polymorphism characterization. As such, polymorphisms may be found in coding regions or untranslated regions of polynucleotides presented in the Sequence Listing, or they may be found within the locus for a disclosed sequence. Polymorphisms that can be identified include simple sequence repeats (SSRs), rapid amplification of polymorphic DNA (RAPDs), amplified fragment length polymorphisms (AFLPs) and restriction fragment length polymorphisms (RFLPs), as described below. If a polymorphism is identified, its presence and frequency in populations is analyzed to determine if it is statistically significantly correlated to a trait, such as the trait noted in the Sequence Listing. Those polymorphisms that are correlated with a trait can be incorporated into a marker assisted breeding program to facilitate the development of lines that have a desired alteration the respective trait. Typically, a polymorphism identified in such a manner is used with polymorphisms at other loci that are correlated with the same trait.

The use of RFLPs and of recombinant inbred lines for such genetic mapping is described for *Arabidopsis* by Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.) and for corn by Burr ("Mapping Genes with Recombinant Inbreds", pp. 249-254. In Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; Gardiner, J. et al., (1993) *Genetics* 134: 917). This procedure, however, is not limited to plants and is used for other organisms (such as yeast) or for individual cells.

The polynucleotides of the present invention are also used for simple sequence repeat (SSR) mapping. Rice SSR mapping is described by Morgante et al. (*The Plant Journal* (1993) 3: 165), Panaud et al. (*Genome* (1995) 38: 1170); Senior et al. (*Crop Science* (1996) 36: 1676), Taramino et al. (*Genome* (1996) 39: 277) and Ahn et al. (*Molecular and General Genetics* (1993) 241: 483-90). SSR mapping is achieved using various methods. In one instance, polymorphisms are identified when sequence specific probes contained within a polynucleotide flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms are identified by using the PCR fragment produced from the SSR-flanking sequence specific primer reaction as a probe against Southern blots representing different individuals (U. H. Refseth et al., (1997) *Electrophoresis* 18: 1519).

The polynucleotides of the invention can further be used to identify certain genes or genetic traits using, for example, known AFLP technologies, such as in EP0534858 and U.S. Pat. No. 5,878,215.

The polynucleotides of the present invention are also used for single nucleotide polymorphism (SNP) mapping.

The polynucleotides of the invention can be used with the various types of maps discussed above to identify Quantitative Trait Loci (QTLs). Many important crop traits, such as the solids content of tomatoes, are quantitative traits and result from the combined interactions of several genes. These genes reside at different loci in the genome, often times on different chromosomes, and generally exhibit multiple alleles at each locus. The polynucleotides of the invention are used to identify QTLs and isolate specific alleles as described by de Vicente and Tanksley (*Genetics* (1993) 4:585). Once a desired allele combination is identified, crop improvement is accomplished either through biotechnological means or by directed conventional breeding programs (for review see Tanksley and McCouch (1997) *Science* 277:1063). In addition to isolating QTL alleles in present crop species, the polynucleotides of the invention are also used to isolate alleles from the corresponding QTL of wild relatives.

In addition, the polynucleotides of the present invention can be used for marker assisted breeding. Marker assisted breeding uses genetic fingerprinting techniques to assist plant breeders in matching a molecular profile to the physical properties of a variety. This allows plant breeders to significantly accelerate the speed of natural plant breeding programs. Marker assisted breeding also allows better retention of sequences that participate in QTLs.

Following the procedures described above and using a plurality of the polynucleotides of the present invention, any individual can be genotyped. These individual genotypes are used for the identification of particular cultivars, varieties, lines, ecotypes and genetically modified plants or can serve as tools for subsequent genetic studies directed towards the improvement of multiple phenotypic traits.

4. The Sequences of the Invention

Polynucleotides of the present invention and proteins expressed via translation of these polynucleotides are set forth in the Sequence Listing, specifically the polynucleotides from *Panicum virgatum*. The Sequence Listing also provides annotations which are indicative of use(s) for which the sequences can be utilized; for example, to make transgenic plants with modulated growth and phenotype characteristics, including ornamental, biomass and seed yield, confinement, stress tolerance, ornamental and/or compositional characteristics.

5. Use of the Sequences to Make Transgenic Plants

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, Sambrook et al., Molecular Cloning: A Laboratory Manual, Second Edition, Cold Spring Harbor Laboratory Press (1989) New York) and can be introduced into the plant species of interest by, for example, *Agrobacterium*-mediated transformation, or by other means of transformation, for example, as disclosed below.

The vector backbone may be any of those typically used in the field such as plasmids, viruses, artificial chromosomes, BACs, YACs, PACs and vectors such as, for instance, bacteria-yeast shuttle vectors, lamda phage vectors, T-DNA fusion vectors and plasmid vectors (see, 17-24).

Typically, the construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorsulfuron or phosphinothricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence.

To "operably link" a promoter sequence to a sequence, the translation initiation site of the translational reading frame of said sequence is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *Plant Cell* 1:977-984.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al. (1989) *Plant Cell* 1:855-866; Bustos et al. (1989) *Plant Cell* 1:839-854; Green et al. (1988) *EMBO J.* 7: 4035-4044; Meier et al. (1991) *Plant Cell* 3: 309-316; and Zhang et al. (1996) *Plant Physiology* 110: 1069-1079.

Examples of various classes of regulatory regions are described below. Some properties of the regulatory regions indicated below, as well as additional regulatory regions, are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/034308; and PCT/US05/23639. Specifically, the sequences of regulatory regions p326, YP0144, YP0190, p13879, YP0050, p32449, 21876, YP0158, YP0214, YP0380, PT0848, PT0633 YP0128, YP0275, PT0660, PT0683, PT0758, P70613, PT0672, P70837, YP0092, PT0676, PT0708, YP0396, YP0007, YPO111, YP0103, YP0028, YP0121, YP0008, YP0039, YP0115, YPO19, YP0120, YP0374, YP0039, YP01, YP0102, YPO110, YP0117, YP0119, YP0137, YP0285, YP0212, YP0097, YP0107, YP0088, YP0143, YP0156, PT0650, PT0695, PT0723, P0838, PT0879, PT0740, PT0535, PT0668, PT0886, PT0585, YP0381, YP0337, YP0374, PT0710, YP0356, YP0385, YP0396, YP0384, PT0688, YP0286, YP0377, PD1367, PT0863, P0829, PT0665, PT0678, YP0086, YP0188, YP0263, PT0758, PT0743, PT0829, YP0119, and YP0096 are set forth in the sequence listing of PCT/US06/040572; the sequence of regulatory region PT0625 is set forth in the sequence listing of PCT/US05/034343; the sequences of regulatory regions P70623, YP0388, YP0087, YP0093, YP0108, YP0022, and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236. It will be appreciated that a regulatory region may meet criteria for one classification based on its activity in one plant species, and yet meet criteria for a different classification based on its activity in another plant species.

Broadly Expressing Promoters: A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root Promoters: Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

Maturing Endosperm Promoters: In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

Ovary Tissue Promoters: Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YPO111, YP0092, YP0103, YP0028, YP0121, YP0008, YP0039, YP0115, YPO19, YP0120, and YP0374.

Embryo Sac/Early Endosperm Promoters: To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters. Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096);

and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOs-FIE2-2, pOsMEA, pOsYp102, and pOsYp285.

Embryo Promoters: Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

Photosynthetic Tissue Promoters: Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cabl R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcbl*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include Ff0535, FT0668, PT0886, YP0144, YP0380 and FT0585.

Vascular Tissue Promoters: Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

Inducible Promoters: Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, P0633, YP0374, PT0710, YP0356, YP0385, YP0396, YP0388, YP0384, FT0688, YP0286, YP0377, and PD1367. Examples of nitrogen-inducible promoters include PT0863, PT0829, PT0665, and FT0886. Examples of shade-inducible promoters include PR0924 and PT0678. An example of a promoter induced by salt is rd29A (Kasuga et al. (1999) *Nature Biotech* 17: 287-291).

Basal Promoters: A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters: Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, T0758, FT0743, FT0829, YP0119, and YP0096, as described in the above-referenced patent applications, may also be useful.

Other Regulatory Regions: A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence. It will be understood that more than one regulatory region may be present in a recombinant polynucleotide, e.g., introns, enhancers, upstream activation regions, transcription terminators, and inducible elements.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant (US patent publication 20050257293A1). In another alternative embodiment of the present invention, the misexpression can be accomplished by having the sequences of the two component system transformed in one transgenic plant line.

Another alternative consists in inhibiting expression of a growth or phenotype-modulating polypeptide in a plant species of interest. The term "expression" refers to the process of converting genetic information encoded in a polynucleotide into RNA through transcription of the polynucleotide (i.e., via the enzymatic action of an RNA polymerase), and into protein, through translation of mRNA. "Up-regulation" or "activation" refers to regulation that increases the production of expression products relative to basal or native states, while "down-regulation" or "repression" refers to regulation that decreases production relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not complement the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used (e.g., at least 40, 50, 80, 100, 200, 500 nucleotides or more).

Thus, for example, an isolated nucleic acid provided herein can be an antisense nucleic acid to one of the aforementioned nucleic acids encoding a growth or phenotype-modulating polypeptide. A nucleic acid that decreases the level of a transcription or translation product of a gene encoding a growth or phenotype-modulating polypeptide is transcribed into an antisense nucleic acid, or complementary to the coding sequence of the growth or phenotype-modulating polypeptide in the Sequence Lisitng. Alternatively, the transcription product of an isolated nucleic acid can be similar or complementary to the coding sequence of a growth or phenotype-modulating polypeptide in the Sequence Listing, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in Tetrahymena *thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the growth or phenotype-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; Hyrup et al. (1996) *Bioorgan. Med. Chem.*, 4: 5-23. In addition, the deoxyphosphate backbone can be replaced with, for example, a phosphorothioate or phosphorodithioate backbone, a phosphoroamidite, or an alkyl phosphotriester backbone.

In some cases, expression of a polypeptide of the invention inhibits one or more functions of an endogenous polypeptide. For example, a nucleic acid that encodes a dominant negative polypeptide can be used to inhibit gene function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation Transformation Nucleic acid molecules of the present invention may be introduced into the genome or the cell of the appropriate host plant by a variety of techniques. These techniques, able to transform a wide variety of higher plant species, are well known and described in the technical and scientific literature (see, e.g., 28-29).

A variety of techniques known in the art are available for the introduction of DNA into a plant host cell. These techniques include transformation of plant cells by injection (30), microinjection (31), electroporation of DNA (32), PEG (33), use of biolistics (34), fusion of cells or protoplasts (35), and via T-DNA using *Agrobacterium tumefaciens* (36-37) or *Agrobacterium rhizogenes* (38) or other bacterial hosts (39), for example.

In addition, a number of non-stable transformation methods that are well known to those skilled in the art may be desirable for the present invention. Such methods include, but are not limited to, transient expression (40) and viral transfection (41).

Seeds are obtained from the transformed plants and used for testing stability and inheritance. Generally, two or more generations are cultivated to ensure that the phenotypic feature is stably maintained and transmitted.

A person of ordinary skill in the art recognizes that after the expression cassette is stably incorporated in transgenic plants and confirmed to be operable, it can be introduced into other plants by sexual crossing. Any of a number of standard breeding techniques can be used, depending upon the species to be crossed.

The methods according to the present invention can be applied to any plant, preferably higher plants, pertaining to the classes of Angiospermae and Gymnospermae. Plants of the subclasses of the Dicotylodenae and the Monocotyledonae are particularly suitable. Suitable species may come from the family Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, and Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

The methods of the present invention are preferably used in plants that are important or interesting for agriculture, horticulture, biomass for the production of liquid fuel molecules and other chemicals, and/or forestry. Non-limiting examples include, for instance, *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine mar* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Arundo donax* (giant reed), *Secale cereale* (rye), *Salix* spp. (willow), *Eucalyptus* spp. (eucalyptus), *Triticosecale* spp. (*triticum*-wheat X rye), Bamboo, *Carthamus tinctorius* (safflower), *Jatropha curas* (jatropha), *Ricinus communis* (castor), *Elaeis guineensis* (palm), *Linum usitatissimum* (flax), *Brassica juncea, Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum calfornica., Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum* coca, *Galanthus wornorii, Scopolia* spp., *Lycopodium serratum* (=*Huperzia serrata*), *Lycopodium* spp., *Rauwolfa serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers. Of interest are plants grown for energy production, so called energy crops, such as cellulose-based energy crops like *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Andropogon* gerardii (big bluestem), *Pennisetum purpureum* (elephant grass), *Phalaris arundinacea* (reed canarygrass), *Cynodon dactylon*

(bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), Triticosecale spp. (*triticum*-wheat X rye), and Bamboo; and starch-based energy crops like *Zea mays* (corn) and *Manihot esculenta* (cassava); and sucrose-based energy crops like *Saccharum* sp. (sugarcane) and *Beta vulgaris* (sugarbeet); and biodiesel-producing energy crops like *Glycine max* (soybean), *Brassica napus* (canola), *Helianthus annuus* (sunflower), *Carthamus tinctorius* (safflower), *Jatropha curcas* (*jatropha*), *Ricinus communis* (castor), *Elaeis guineensis* (palm), *Linum usitatissimum* (flax), and *Brassica juncea*. Thus, the described materials and methods are useful for modifying biomass characteristics, such as characteristics of biomass renewable energy source plants. A biomass renewable energy source plant is a plant having or producing material (either raw or processed) that comprises stored solar energy that can be converted to electrical energy, liquid fuels, and other useful chemicals. In general terms, such plants comprise dedicated energy crops as well as agricultural and woody plants. Examples of biomass renewable energy source plants include: *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), Triticosecale spp. (*triticum*-wheat X rye), Bamboo, *Zea mays* (corn), *Manihot esculenta* (cassava), *Saccharum* sp. (sugarcane), *Beta vulgaris* (sugarbeet), *Glycine max* (soybean), *Brassica napus* (canola), *Helianthus annuus* (sunflower), *Carthamus tinctorius* (safflower), *Jatropha curcas* (*jatropha*), *Ricinus communis* (castor), *Elaeis guineensis* (palm), *Linum usitatissimum* (flax), and *Brassica juncea*.

Homologues Encompassed by the Invention

It is known in the art that one or more amino acids in a sequence can be substituted with other amino acid(s), the charge and polarity of which are similar to that of the substituted amino acid, i.e. a conservative amino acid substitution, resulting in a biologically/functionally silent change. Conservative substitutes for an amino acid within the polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

Nucleic acid molecules of the present invention can comprise sequences that differ from those encoding a protein or fragment thereof selected from the group consisting of the nucleotide sequences in the sequence listing due to the fact that the different nucleic acid sequence encodes a protein having one or more conservative amino acid changes.

Biologically functional equivalents of the polypeptides, or fragments thereof, of the present invention can have about 10 or fewer conservative amino acid changes, more preferably about 7 or fewer conservative amino acid changes, and most preferably about 5 or fewer conservative amino acid changes. In a preferred embodiment of the present invention, the polypeptide has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleic Acid Molecules and Their Corresponding Nucleotide Sequences The nucleic acid molecules and nucleotide sequences thereof of the present invention were identified as functional homologs of other sequences of established function and utility. The other sequences and their established function come from public and proprietary sources. For example, in some cases the properties of these sequences were established by use of a variety of screens that are predictive of nucleotide sequences that provide plants with altered size, vegetative growth, organ number, plant architecture, biomass, and/or enhanced resistance to various abiotic or biotic stresses. In other cases, characteristics of similar sequences are known from scientific and technical literature readily accessible to those of skill in the art.

Functional homologs/orthologs from *Panicum virgatum* for each gene of interest, which in many cases may be capable of modulating growth and phenotype characteristic when transformed in plants. The "Determination of Functional Homolog/Ortholog Sequences" process described below can be used to identify functional homologs/orthologs. Functional homologs/orthologs of a sequence of interest are understood to affect similar phenotype(s) as observed for the respective sequence of interest when their expression is modulated in plants.

Determination of Functional Homolog/Ortholog Sequences

A subject sequence is considered a functional homolog or ortholog of a query sequence if the subject and query sequences encode proteins having a similar function and/or activity. A process known as Reciprocal BLAST (Rivera et al., *Proc. Natl. Acad. Sci. USA*, 95:6239-6244 (1998)) was used, for many of the sequences provided, to identify potential functional homolog and/or ortholog sequences from a database consisting of Ceres-Inc. proprietary peptide sequences from *Panicum virgatum*.

Before starting a Reciprocal BLAST process, a specific query polypeptide is searched against all peptides from its source species using BLAST in order to identify polypeptides having BLAST sequence identity of 80% or greater to the query polypeptide and an alignment length of 85% or greater along the shorter sequence in the alignment. The query polypeptide and any of the aforementioned identified polypeptides are designated as a cluster.

The BLASTP version 2.0 program from Washington University at Saint Louis, Mo., USA is used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity is calculated based on the alignment of the first BLAST HSP (High-scoring Segment Pairs) of the identified potential functional homolog and/or ortholog sequence with a specific query polypeptide. The number of identically matched residues in the BLAST HSP alignment is divided by the HSP length, and then multiplied by 100 to get the BLAST sequence identity. The HSP length typically includes gaps in the alignment, but in some cases gaps can be excluded.

The main Reciprocal BLAST process consists of two rounds of BLAST searches; forward search and reverse search. In the forward search step, a query polypeptide sequence, "polypeptide A," from source species SA (such as *Arabidopsis*) is BLASTed against all Ceres-Inc. proprietary peptide sequences from *Panicum virgatum*. Top hits are determined using an E-value cutoff of 10-5 and a sequence identity cutoff of 35%. Among the top hits, the sequence having the lowest E-value is designated as the best hit, and considered a potential functional homolog or ortholog. Any other top hit that has a high BLAST sequence identity to the best hit or to the original query polypeptide is considered a potential functional homolog or ortholog as well.

In the reverse search round, the top hits identified in the forward search from *Panicum virgatum* are BLASTed against all protein sequences from the source species SA. A top hit from the forward search that returns a polypeptide from the aforementioned cluster as its best hit is also considered as a potential functional homolog or ortholog.

Functional homologs and/or orthologs are identified by manual inspection of potential functional homolog and/or ortholog sequences. In some cases identification is based on known correlations between sequence domains and functions for specific classes of biomolecules.

Information in the Sequence Listing

The switchgrass sequences provided in the Sequence Listing are annotated to indicate one or several potential applications of the respective sequences. Some sequences are enzymes, i.e. catalysts of specific chemical or biochemical reactions, and their activity is indicated by enzyme classification (EC) numbers. The EC numbers used in the sequence listing correspond to the swissprot enzyme classification system, as found on the World Wide Web. Some sequences contain "pfam" domains which are indicative of particular applications. The specific pfam domains are described in more detail by various sources on the World Wide Web.

Some switchgrass sequences in the Sequence Listing are annotated in the "miscellaneous features" section as functional homologs of known sequences, and associated traits that could be modulated by the respective sequences in transgenic plants. In this context "great-hit" denotes a BLAST hit from a forward search that returns a polypeptide from the query cluster as its best hit in the reverse BLAST search, as explained above. Known sequence-function associations are sometimes based at least in part on literature documentation. In some cases, the known query sequences are not reproduced in the sequence listing, but it is identified by literature reference, such as by reference to specific sequences in patent publications or *Arabidopsis* locus numbers. If desired, sequence information for these designations may be obtained from various sources, such as the EMBL sequence database or *Arabidopsis* database available on the World Wide Web. In some cases, query sequences such as SEQ ID NOs: 9177-9762 are provided in the sequence listing, along with information pertinent to observed transgenic plant traits. When a listed query sequence is a truncation of a known coding region, those of skill in the art could design if necessary an equivalent truncation of the corresponding switchgrass functional homologs to obtain the indicated phenotype.

Modulated growth and phenotype characteristics for some of the sequences of the invention are noted by entries in the "miscellaneous feature" section for the respective nucleic acid and/or polypeptide sequence in the Sequence Listing. Valuable applications of the respective sequences are also sometimes noted in the Sequence Listing. In many cases, traits were originally associated with known sequences by misexpression or other transgenic or genetic interference with specific gene functions. For some sequences, plants were transformed with the genes of interest and screened for modulated morphological characteristics, as described, for example in PCT/US2005023326 or PCT/US2005/047099. When applicable, phenotypic observations for transformants are noted in the Sequence Listing. For some sequences, transgenic trait associations were suggested by results of screening transgenic plants for tolerance to specific stress conditions. Screening procedures and some results are exemplified in PCT/US2005/018950, PCT/US2005/018912, PCT/US2005/014197, or PCT/US2006/040572. Other methods are exemplified by references cited in the Sequence Listing or below.

From the disclosure of the Sequence Listing, it can be seen that the nucleotides and polypeptides of the inventions are useful, depending upon the respective individual sequence, to make plants with one or more altered characteristics in traits. For example, the sequences can be used, as noted in the sequence listing for the respective sequences, for biocontainment applications, for making ornamental plants with delayed petal abscission, alkaloid content, amino acid content, carbohydrate content, carbon content, carotene content, cell wall content and/or composition, glycerol content, lignin content, lutein content, lycopene content, nitrogen content, oil content, protein content, sterol content, terpenoid content, tocopherol content, enhanced nutritional value, high aluminum sensitivity, abiotic stress sensitivity, abscission, asexual embryo production, biomass, biotic stress sensitivity, carbohydrate content, carbon-nitrogen partitioning, cold sensitivity, drought sensitivity, endosperm cell number, endosperm cell size, endosperm size, flowering time, growth rate, heat sensitivity, herbicide sensitivity, high pH sensitivity, light quality response, light quality sensitivity, light response, light sensitivity, low iron sensitivity, low light sensitivity, nitrogen use efficiency, oxidative stress sensitivity, phosphate use efficiency, plant growth and development, root development, salt sensitivity, seed content, seed number, seed quality, seed size, seedling growth, silicon content, time to senescence, UV sensitivity, water use efficiency, yield.

Additionally, clone ids 1986288 (SEQ ID NO: 8028) and 1792286 (SEQ ID NO: 3570), are "useful for making plants with modulated flowering time." Furthermore, clone ids 1769278 (SEQ ID NO: 1674), 1797688 (SEQ ID NO: 4222), and 1891486 (SEQ ID NO: 6912) are "useful for making plants with modulated drought sensitivity."

Nucleotides and polypeptides that are useful for modulating plant characteristics in traits such as sterility, lethality and/or viability have been noted as "useful for biocontainment applications" or "useful for making plants with modulated asexual embryo production" in the Sequence Listing. Nucleotides and polypeptides that with this designation include those that are able to confer one or more of the following phenotypes, relative to wild-type control, when mis-expressed in plants: increased or decreased number of floral organs; alter floral organ type; reduced fertility; sterility, including female-sterility and/or male-sterility; alter how leaves emerge from the meristem; low/no seed germination; and reduced plant viability (e.g. albino plants and plants with vitrified leaves). The ability to modulate sterility, lethality, and/or viability is important in developing a genetic confinement system designed to reduce or prevent gene flow from transgenic pants to commercial crops and wild-type counterparts, making ornamental plants; and for other agricultural and/or horticultural purposes. Nucleotides and polynucleotides useful for developing a genetic confinement system can be utilized by procedures known to those skilled in the art, such as in US2005/0257293 A1, hereby incorporated by reference.

Some nucleotides and polypeptides are noted as being "useful for making plants with modulated biomass", "useful for making plants with modulated yield", "useful for making plants with modulated flowering time," "useful for making plants with modulated seed size", "useful for making plants with modulated time to senescence", "useful for making plants with modulated endosperm cell number", "useful for making plants with modulated endosperm cell size", "useful for making plants with modulated endosperm size", "useful for making plants with modulated growth rate", "useful for making plants with modulated seed content", "useful for making plants with modulated seed number", "useful for making plants with modulated seed quality", "useful for making plants with modulated plant growth and development." or "useful for making plants with modulated seedling growth" in the Sequence Listing. Nucleotides and polypeptides that have been given these designation include those that are able to confer one or more of the following phenotypes, relative to wild-type control, when mis-expressed in plants: increased or decreased plant size; increased or decreased plant height; increased or decreased leaf size; altered leaf shape; altered leaf structure; increased or decreased number of leaves; increased or decreased organ size; altered organ shape; increased or decreased organ number, increased or decreased branching length; increased or decreased branch number, increase or decrease petal abscission, increase or decrease in leaf abscission, increased or decreased apical dominance; and increased or decreased hypocotyls length. Altering plant biomass is valuable for increasing plant biomass produced per acre of arable land, increasing crop yield per acre of arable land, utilizing plants as chemical factories to produce valuable pharmaceutical compounds, developing a genetic confinement system designed to reduce or prevent gene flow from transgenic plants to commercial crops and wild-type counterparts, making ornamental plants; and for other agricultural and/or horticultural purposes.

Some nucleotides and polypeptides that are useful for modulating plant characteristics in traits such as the composition of a plant, plant material, plant tissue, plant cell and seed from a plant include those that have been given the designations "useful for making plants with altered alkaloid content", "useful for making plants with altered carbon content", "useful for making plants with modulated carbon-nitrogen partitioning", "useful for making plants with altered carotene content", "useful for making plants with modulated carbohydrate content", "useful for making plants with altered carbohydrate content", "useful for making plants with altered cell wall content and/or composition", "useful for making plants with altered glycerol content", "useful for making plants with altered lignin content", "useful for making plants with altered lutein content", "useful for making plants with altered lycopene content", "useful for making plants with altered nitrogen content", "useful for making plants with altered oil content", "useful for making plants with altered protein content", "useful for making plants with altered amino acid content", "useful for making plants with altered sterol content", "useful for making plants with altered terpenoid content", "useful for making plants with altered tocopherol content", "useful for making plants with modulated silicon content", or "useful for making plants with enhanced nutritional value" in the Sequence Listing. Nucleotides and polypeptides that have been given these designations include those that are able to confer one or more of the following phenotypes, relative to wild-type control, when mis-expressed in plants: increased or decreased carbon content; increased or decreased plant nitrogen content; altered color (indicative of change(s) to the chemical composition); altered metabolic profile, increased or decreased starch content, increased or decreased fiber content; increased or decreased amount of a valuable compound (e.g. increased alkaloids and/or terpenoids); increased or decreased number of trichomes; increased or decreased cotyledon size; increased or decreased cotyledon number; altered cotyledon shape; increased or decreased fruit size; increased or decreased fruit length; altered fruit shape; increased or decreased seed size; and altered seed shape; altered seed color (indicative of altered chemical composition); and having activated expression of a gene operably linked to an alkaloid or terpenoid related regulatory region or promoter. Altering characteristics such as the composition of a plant, plant organ, plant tissue and plant cell is valuable for improving the nutritional value of crops, improving the composition of plants to be used as bio-fuels, utilizing plants as chemical factories by increasing the content of valuable pharmaceutical compounds, producing plants with increased tolerance to abiotic or biotic stress, developing a genetic confinement system designed to reduce or prevent gene flow from transgenic plants to commercial crops and wild-type counterparts, making ornamental plants, and for other agricultural and/or horticultural purposes. Nucleotides and polynucleotides useful for developing plants with modified compositions can be utilized by procedures known to those skilled in the art, such as in PCT/US2006/014161, PCT/US2005/032680, PCT/US2006/0022851, PCT/US2005/44112, PCT/US2005/043562, PCT/US2006/41516, U.S. Ser. No. 60/838,646, U.S. Ser. No. 60/855,108, U.S. Ser. No. 60/854,825 PCT/US2006/360,459, PCT/US2007/061052, and PCT/US2007/002214, hereby incorporated by reference.

Some nucleotides and polypeptides that are useful for modulating plant characteristics in traits such as phosphate use include those that have been given the designation "Useful for making plants with modulated phosphate use efficiency", "useful for making plants with modulated high pH sensitivity", or "useful for making plants with high aluminum sensitivity", in the Sequence Listing. Nucleotides and polypeptides that have been given these designations include those that are able to confer one or more of the following phenotypes, relative to wild-type control, when mis-expressed in plants: increased or decreased tolerance to low phosphate conditions; increased or decreased tolerance to no phosphate conditions, and increased or decreased tolerance to high pH conditions. Altering characteristics such as phosphate use through genetic technologies is valuable for producing crop plants with increased tolerance to phosphate limiting conditions, using traditionally un-arable land to grow crop plants with increased tolerance to phosphate limiting conditions, developing a genetic confinement system designed to reduce or prevent gene flow from transgenic plants to commercial crops and wild-type counterparts, and for other agricultural and/or horticultural purposes. Nucleotides and polynucleotides useful for developing plants with modulated phosphate use efficiency can be utilized by procedures known to those skilled in the art, such as in PCT/US2005/018912, hereby incorporated by reference.

Nucleotides and polypeptides that are useful for modulating plant characteristics in traits such as light responses include those that have been given the designations "useful for making plants with modulated light quality response", "useful for making plants with modulated light quality sensitivity", "useful for making plants with modulated light response", "useful for making plants with modulated light sensitivity", "useful for making plants with modulated UV sensitivity", "useful for making plants with modulated low light sensitivity" in the Sequence Listing. Nucleotides and polypeptides that have been given these designations include those that are able to confer one or more of the following phenotypes, relative to wild-type control, when mis-expressed in plants: increased or decreased vigor in the dark; increased or decreased seedling vigor under low light conditions; increased or decreased plant vigor under low light conditions; increased or decreased leaf length; altered leaf shape; altered leaf structure, and increased or decreased cotyledon length. Altering characteristics such as shade avoidance and shade tolerance through genetic technologies is valuable for producing plants with tolerance to light limiting conditions, increasing plant biomass produced per acre of arable land, increasing crop production per acre of arable land, developing a genetic confinement system designed to reduce or prevent gene flow from transgenic plants to commercial crops and wild-type counterparts, making ornamental plants, and for other agricultural and/or horticultural purposes. Nucleotides and polynucleotides useful for developing plants with light responses can be utilized by procedures known to those skilled in the art, such as in U.S. Ser. No. 60/799,404, U.S. Ser. No. 60/813,533, and U.S. Ser. No. 60/818,569, hereby incorporated by reference.

Nucleotides and polypeptides that are useful for modulating plant characteristics in traits such as nitrogen use include those that have been given the designation "Useful for making plants with modulated nitrogen use efficiency" in the Sequence Listing. Nucleotides and polypeptides that have been given the "Nitrogen use" designation include those that are able to confer one or more of the following phenotypes, relative to wild-type control, when mis-expressed in plants: increased or decreased tolerance to low nitrogen conditions and surrogate low nitrogen conditions (e.g. exposure to an effective amount of MSX); increased or decreased tolerance to no nitrogen conditions; increased tolerance to high nitrogen conditions. Altering nitrogen use through genetic technologies is valuable for producing plants with increased tolerance to high or low nitrogen conditions, decreasing the amount of fertilizers used in crop production, using traditionally un-arable land to grow crop plants with increased tolerance to high or low nitrogen conditions, developing a genetic confinement system designed to reduce or prevent gene flow from transgenic plants to commercial crops and wild-type counterparts, and for other agricultural and/or horticultural purposes. Nucleotides and polynucleotides useful for developing plants with improved nitrogen use efficiency can be utilized by procedures known to those skilled in the art, such as in PCT/US2005/014197, hereby incorporated by reference.

Nucleotides and polypeptides that are useful for modulating plant characteristics in traits such as stress tolerance include those that have been given the designations "useful for making plants with modulated cold sensitivity", "useful for making plants with modulated drought sensitivity", "useful for making plants with modulated heat sensitivity", "useful for making plants with modulated low iron sensitivity", "useful for making plants with modulated oxidative stress sensitivity", "useful for making plants with modulated root development", "useful for making plants with modulated water use efficiency", "useful for making plants with modulated salt sensitivity", "useful for making plants with modulated abiotic stress sensitivity", or "useful for making plants with modulated biotic stress sensitivity" in the Sequence Listing. Nucleotides and polypeptides that have been given these designation include those that are able to confer one or more of the following phenotypes, relative to wild-type control, when mis-expressed in plants: increased or decreased tolerance to drought and/or surrogate drought conditions (e.g. exposure to effective amounts of ABA, PEG, mannitol or sucrose); increased or decreased tolerance to low temperature conditions; increased or decreased tolerance to high temperature conditions; increased or decreased salt tolerance; increased or decreased tolerance to oxidative stressors and/or surrogate oxidative stressors (e.g. exposure to an effective amount of arginine, ozone, or salicylic acid); having leaves with shiny or dull appearance (indicative of altered wax composition and/or content); and increase or decrease pest resistance. Altering abiotic stress tolerance through genetic technologies is valuable for farmers seeking to minimize economic losses due to drought, cold, heat, flooding and oxidative stressors; producing crop plants with increased tolerance to abiotic stressors; using traditionally un-arable land to grow crop plants with increased tolerance to abiotic stressors; developing a genetic confinement system designed to reduce or prevent gene flow from transgenic plants to commercial crops and wild-type counterparts; making ornamental plants; and for other agricultural and/or horticultural purposes. Nucleotides and polynucleotides useful for developing plants with improved abiotic stress tolerance can be utilized by procedures known to those skilled in the art, such as in PCT/US2005/018950, U.S. Ser. No. 11/248,547, U.S. Ser. No. 60/837,434, U.S. Ser. No. 60/860,296, or U.S. Ser. No. 60/851,585, hereby incorporated by reference.

The phenotypes mentioned in the sequence listing can be modulated by controlling the expression of nucleic acid sequences and polypeptide sequences that confer phenotype(s) when mis-expressed in plants. Modulation of a phenotype can also be achieved by inhibiting the expression of nucleic acid sequences and polypeptide sequences that confer phenotype(s) when mis-expressed in plants. A phenotype resulting from the expression of a nucleic acid sequence and/or polypeptide sequence can be modulated (e.g. increase or decrease of an observable/measurable phenotypic change in relation to wild-type control) using recombinant-DNA methods, as discussed in previous paragraphs.

According to another aspect, the nucleotide sequences of the invention encode polypeptides that can be utilized as herbicide targets, those useful in the screening of new herbicide compounds. Thus, the proteins encoded by the nucleotide sequences provide the bases for assays designed to easily and rapidly identify novel herbicides.

According to yet another aspect, the present invention provides a method of identifying a herbicidal compound, comprising: (a) combining a polypeptide comprising an amino acid sequence at least 85% identical to an amino acid sequence selected from the group consisting of the polypeptides described in the sequence listing with a compound to be tested for the ability to inhibit the activity of said polypeptide, under conditions conducive to inhibition; (b) selecting a compound identified in (a) that inhibits the activity of said polypeptide; (c) applying a compound selected in (b) to a plant to test for herbicidal activity; (d) selecting a compound identified in (c) that has herbicidal activity. The polypeptide can alternatively comprise an amino acid sequence at least 90%, or at least 95%, or at least 99% identical to an amino acid sequence selected from the group consisting of the polypeptides in the sequence listing. The present invention also provides a method for killing or inhibiting the growth or viability of a plant, comprising applying to the plant a herbicidal compound identified according to this method.

The Sequence Listing sets forth the polypeptide and polynucleotide sequences of the invention, including, in many cases, functional homologs of specific query sequences. The Sequence Listing indicates which of the functional homologs are associated with each query sequence. Sequencing reads from the same clone are given the same clone id number. The 3' read of a clone will additionally have the "R" designation. Overlapped clones and 5' reads of a clone do not have the "R" designation."

The present invention further encompasses nucleotides that encode the above described polypeptides, such as those included in the sequence listing, as well as the complements and/or fragments thereof, and including alternatives thereof based upon the degeneracy of the genetic code.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

REFERENCES (1) Zhang et al. (2004) *Plant Physiol.* 135:615.
(2) Salomon et al. (1984) *EMBO J.* 3:141.
(3) Herrera-Estrella et al. (1983) *EMBO J.* 2:987.
(4) Escudero et al. (1996) *Plant J.* 10:355.
(5) Ishida et al. (1996) *Nature Biotechnology* 14:745.
(6) May et al. (1995) *Bio/Technology* 13:486)
(7) Armaleo et al. (1990) *Current Genetics* 17:97.
(8) Smith. T. F. and Waterman, M. S. (1981)*Adv. App. Math.* 2:482.
(9) Needleman and Wunsch (1970) *J. Mol. Biol.* 48:443.
(10) Pearson and Lipman (1988) *Proc. Nat. Acad Sci.* (UA) 85: 2444.
(11) Yamauchi et al. (1996) *Plant Mol Biol.* 30:321-9.
(12) Xu et al. (1995) *Plant Mol. Biol.* 27:237.
(13) Yamamoto et al. (1991) *Plant Cell* 3:371.
(14) P. Tijessen, "Hybridization with Nucleic Acid Probes" In Laboratory Techniques in Biochemistry and Molecular Biology, P. C. vand der Vliet, ed., c. 1993 by Elsevier, Amsterdam.
(15) Bonner et al., (1973) *J. Mol. Biol.* 81:123.
(16) Sambrook et al., *Molecular Cloning: A Laboratory Manual*, Second Edition, Cold Spring Harbor Laboratory Press, 1989, New York.
(17) Shizuya et al. (1992) *Proc. Nal. Acad. Sci. USA,* 89: 8794-8797.
(18) Hamilton et al. (1996) *Proc. Nal. Acad. Sci. USA,* 93: 9975-9979.
(19) Burke et al. (1987) *Science,* 236:806-812.
(20) Sternberg N. et al. (1990) *Proc Natl. Acad Sci USA.,* 87:103-7.
(21) Bradshaw et al. (1995) *Nucl Acids Res,* 23: 4850-4856.
(22) Frischauf et al. (1983) *J. Mol Biol,* 170: 827-842.
(23) Huynh et al., Glover N M (ed) DNA Cloning: A practical Approach, Vol. 1 Oxford: IRL Press (1985).
(24) Walden et al. (1990) *Mol Cell Biol* 1: 175-194.
(25) Vissenberg et al. (2005) *Plant Cell Physiol* 46:192.
(26) Husebye et al. (2002) *Plant Physiol* 128:1180.
(27) Plesch et al. (2001) *Plant J* 28:455.
(28) Weising et al. (1988) *Ann. Rev. Genet.,* 22:421.
(29) Christou (1995) *Euphytica,* v. 85, n. 1-3:13-27.
(30) Newell (2000)
(31) Griesbach (1987)*Plant Sci.* 50:69-77.
(32) Fromm et al. (1985) *Proc. Natl. Acad Sci. USA* 82:5824.
(33) Paszkowski et al. (1984) *EMBO J.* 3:2717.
(34) Klein et al. (1987) *Nature* 327:773.
(35) Willmitzer, L. (1993) Transgenic Plants. In: iotechnology, A Multi-Volume Comprehensive treatise (H J. Rehm, G. Reed, A. Püler, P. Stadler, eds., Vol. 2, 627-659, VCH Weinheim-New York-Basel-Cambridge).
(36) *Crit. Rev. Plant. Sci.* 4:1-46.
(37) Fromm et al. (1990) *Biotechnology* 8:833-844.
(38) Cho et al. (2000)*Planta* 210:195-204.
(39) Brootghaerts et al. (2005) *Nature* 433:629-633.
(40) Lincoln et al. (1998) *Plant Mol. Biol. Rep.* 16:1-4.
(41) Lacomme et al. (2001), "Genetically Engineered Viruses" (C. J. A. Ring and E. D. Blair, Eds). Pp. 59-99, BIOS Scientific Publishers, Ltd. Oxford, UK.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11001852B1). An electronic copy of the "Sequence Listing" will also be available from the USPTO upon request and payment of the fee set forth in 37 CFR 1.19(b)(3).

What is claimed is:

1. A nucleic acid molecule comprising:
   (a) a nucleotide sequence encoding an amino acid sequence that is at least 95% identical to the amino acid sequence of SEQ ID NO:26620;
   (b) a nucleotide sequence that is at least 95% identical to the nucleotide sequence of SEQ ID NO: 26619;
   (c) a nucleotide sequence encoding the amino acid sequence of SEQ ID NO:26620; or
   (d) a nucleotide sequence comprising the nucleotide sequence of SEQ ID NO: 26619; and wherein the nucleic acid molecule is operably linked to a heterologous regulatory region; wherein the nucleotide sequence encodes a polypeptide that comprises a heavy-metal-associated Pfam domain, and wherein the polypeptide increases drought tolerance when expressed in the plant.

2. A vector, comprising the nucleic acid molecule of claim 1.

3. A method of increasing drought tolerance, said method comprising introducing into a plant cell the nucleic acid molecule according to claim 1, wherein a plant produced from said plant cell has increased drought tolerance as compared to the corresponding level of said characteristic in tissue of a control plant that does not comprise said nucleic acid molecule.

4. The method of claim 3, wherein said regulatory region is a promoter selected from the group consisting of YP0092, PT0676, PT0708, PT0613, PT0678, PT0688, PT0837, the napin promoter, the Arcelin-5 promoter, the phaseolin gene promoter, the soybean trypsin inhibitor promoter, the ACP promoter, the stearoyl-ACP desaturase gene, the soybean a' subunit of 13-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, the barley hordein gene promoter, p326, YP0144, YP0190, p13879, YP0050, p32449,21876, YP0158, YPO214, YP0380, PT0848, PT0633, the cauliflower mosaic virus 35S promoter, the mannopine synthase promoter, the 1' or 2' promoters derived from T-DNA of *Agrobacterium tumefaciens*, the figwort mosaic virus 34S promoter, actin promoters such as the rice actin promoter, ubiquitin promoters such as the maize ubiquitin-1 promoter, ribulose-1,5-bisphosphate carboxylase promoters such as the RbcS promoter from eastern larch (*Larix laricina*), the cab6 promoter, the Cab-1 gene promoter from wheat, the CAB-1 promoter from spinach, the cabl R promoter from rice, the pyruvate orthophosphate dikinase (PPDK) promoter from corn, the tobacco Lhcbl*2 promoter, the *Arabidopsis thaliana* SUC2 sucrose-H+ symporter promoter, and thylakoid membrane protein promoters from spinach (psaD, psaF, psaE, PC, FNR, atpC, atpD, cab, rbcS, PT0535, PT0668, PT0886, PR0924, and PT0585).

5. A plant cell comprising the nucleic acid molecule of claim 1, wherein a plant produced from said plant cell has increased drought tolerance-as compared to a control plant that does not comprise said nucleic acid molecule.

6. A transgenic plant comprising the plant cell of claim 5.

7. Progeny of the plant of claim 6, wherein said progeny comprises said nucleic acid molecule and has increased drought tolerance as compared to a control plant that does not comprise said nucleic acid molecule.

8. Seed from the transgenic plant according to claim 6 wherein said seed comprises said nucleic acid molecule.

9. Vegetative tissue from the transgenic plant according to claim 6, wherein said vegetative tissue comprises said nucleic acid molecule.

10. A food product comprising vegetative tissue from the transgenic plant according to claim 6.

11. A feed product comprising vegetative tissue from the transgenic plant according to claim 6.

12. A method for increasing drought tolerance in a plant, comprising:
(a) transforming a plant with the nucleic acid molecule according to claim 1; and
(b) expressing said nucleotide sequence in said transformed plant, whereby said transformed plant has increased drought tolerance compared to a plant that has not been transformed with said nucleotide sequence.

13. A method for increasing drought tolerance in a plant, said method comprising altering the level of expression in said plant of the nucleic acid molecule according to claim 1.

14. A transgenic plant having increased drought tolerance as compared to a wild-type plant of the same species, wherein the transgenic plant comprises a recombinant polynucleotide comprising the nucleic acid molecule of claim 1, and wherein the polypeptide encoded by said nucleotide sequence confers to the transgenic plant increased drought tolerance as compared to a wild-type plant of the same species.

15. A method for producing a transgenic plant having increased drought tolerance as compared to a wild-type plant of the same species, the method steps comprising:
introducing the nucleic acid molecule of claim 1 into a plant or a cell of a plant to overexpress the encoded polypeptide of the nucleotide sequence; and
selecting the transgenic plant for increased drought tolerance characteristic as compared to the wild-type plant of the same species.

16. The nucleic acid molecule of claim 1, wherien said nucleic acid molecule comprises a nucleotide sequence encoding an amino acid sequence that is at least 95% identical to the amino acid sequence of SEQ ID NO:26620.

17. The nucleic acid molecule of claim 1, wherein said nucleic acid molecule comprises a nucleotide sequence that is at least 95% identical to the nucleotide sequence of SEQ ID NO: 26619.

18. The nucleic acid molecule of claim 1, wherein said nucleic acid molecule comprises a nucleotide sequence encoding the amino acid sequence of SEQ ID NO:26620.

19. The nucleic acid molecule of claim 1, wherein said nucleic acid molecule comprises the nucleotide sequence of SEQ ID NO:26619.

* * * * *